United States Patent [19]

Reilly et al.

[11] Patent Number: 5,225,540
[45] Date of Patent: Jul. 6, 1993

[54] MONOCLONAL ANTIBODIES TO TISSUE PLASMINOGEN ACTIVATOR (T-PA) WHICH PROLONG ITS FUNCTIONAL HALF-LIFE

[75] Inventors: Thomas M. Reilly; Andrew T. Chiu, both of Wilmington, Del.; Robert M. Knabb, Aston, Pa.

[73] Assignee: Du Pont Merck Pharmaceutical Company, Wilmington, Del.

[21] Appl. No.: 186,277

[22] Filed: Apr. 26, 1988

[51] Int. Cl.$^5$ .................. C07K 15/28; A61K 39/395; C12N 5/20

[52] U.S. Cl. .................. 530/388.25; 530/388.26; 530/389.3; 424/85.8; 435/70.21; 435/172.2; 435/240.27; 935/104; 935/107

[58] Field of Search .................. 424/85.8, 88; 435/7, 435/70.21, 172.2, 240.27, 7.9, 7.91, 7.92; 935/103, 104, 107; 530/387.1, 388.26, 388.1, 388.25, 387, 388, 389.3

[56] References Cited

U.S. PATENT DOCUMENTS

| | | | |
|---|---|---|---|
| 4,833,085 | 5/1989 | Schaumann et al. | 435/240.27 |
| 4,891,312 | 1/1990 | Schaumann et al. | 435/7 |
| 5,009,888 | 4/1991 | Dunn | 424/94.3 |

FOREIGN PATENT DOCUMENTS

| | | |
|---|---|---|
| 190711 | 8/1986 | European Pat. Off. . |
| 257010 | 2/1988 | European Pat. Off. . |
| 287187 | 10/1988 | European Pat. Off. . |

OTHER PUBLICATIONS

Schleef, R. R. et al., Characterization of two monoclonal antibodies against human tissue-type plasminogen activator, 1985. *Thromb. Haemostasis* 53(2):170–175.

Reilly, T. M. et al., Characterization of a panel of monoclonal antibodies against human tissue-type plasminogen activator. 1988, *Hybridoma* 7(2):177–184.

Bode, C., et al., Antibody-directed fibrinolysis, 1989, *J. Biol. Chem.* 264(2):944–948.

Reilly, T. M. et al., Monoclonal antibodies to tissue-type plasminogen activator which prolong its clearance in vivo 1989, *Thromb. Haemostasis* 61(2):259–261.

Holvoet et al., Eur. J. Biochem. 158:173–177 (1986).

MacDonald et al., Gene 42:59–67 (1986).

Schleef et al., Thrombosis and Haemostasis 56:328–332 (1986).

Holvoet et al., Blood 69:284–289 (1987).

Levin et al., Proc. Natl. Acad. Sci. USA 80:6804–6808 (1983).

Verstraete et al., Lancet 1:842–847 (1985).

*Primary Examiner*—David L. Lacey
*Assistant Examiner*—Robert D. Budens
*Attorney, Agent, or Firm*—Blair Q. Ferguson; Annette L. Richter

[57] ABSTRACT

High-affinity murine monoclonal antibodies to t-PA were prepared which prolong the in vivo functional half-life of t-PA without decreasing its plasminogen-activator activity.

6 Claims, 3 Drawing Sheets

MONOCLONAL ANTIBODIES TO TISSUE PLASMINOGEN ACTIVATOR (T-PA) WHICH PROLONG ITS FUNCTIONAL HALF-LIFE

FIELD OF THE INVENTION

This invention relates to hybrid cell lines (lymphocyte hybridomas) for the production of monoclonal antibodies to human tissue plasminogen activator (t-PA), to such homogenous monospecific antibodies and their use to prolong the functional half-life of t-PA in mammals.

BACKGROUND OF THE INVENTION

Human tissue-type plasminogen activator (t-PA), a single chain serine protease of Mr 68,000, is a key physiological regulator of fibrinolysis. It converts the zymogen plasminogen into plasmin, the enzyme which degrades the fibrin network of the thrombus (Collen (1980) *Thromb. Haemostasis* 43:77-82; Rijken and Collen (1981) *J. Biol. Chem.* 256:7035-7041). Apparently, in the presence of a clot, both t-PA and plasminogen bind to fibrin and form a ternary complex in which plasminogen is efficiently activated (Holyaerts et al. *J. Biol. Chem.* 257:2912-2929; Ranby (1982) *Biochim. Biophys. Acta* 704:461-469). The affinity of t-PA for fibrin makes t-PA a clot-specific and useful thrombolytic agent (Van de Werf et al. (1984) *Circulation* 69:605-610), which has been approved for human use in the treatment of acute myocardial infarction and is expected to be approved for the treatment of other thrombotic disorders including pulmonary embolism and deep vein thrombosis. T-PA produces limited conversion of plasminogen in the absence of fibrin, so its effects tend to be localized at the site of a thrombus with limited systemic proteolysis. In addition to binding to plasminogen and fibrin, t-PA binds to a fast-acting plasminogen activator inhibitor (PAI-1), which has been identified in blood plasma and in the culture medium of various cells, and which regulates t-PA activity by complexing with and neutralizing the serine protease (Van Mourik et al. (1984) *J. Biol. Chem.* 259:14914-14921; Colucci et al. (1985) *J. Clin. Invest.* 75:818-814; Almer and Ohlin (1987) *Thromb. Research* 47:335-339). PAI-1 is also referred to as PAI in this application.

The turnover of t-PA in plasma is rapid with an in vivo functional half-life of 2 to 6 min, depending on the species (Korninger et al. (1981) *Thromb. Haemostasis* 46:658-661; Verstraete et al. (1985) *J. Pharmacol. Exp. Ther.* 235:506-512). Exogenously introduced t-PA is rapidly taken up and accumulated in the liver (Fuchs et al. (1985) *Blood* 65:539-544; Emeis et al. (1985) *Thromb. Haemostasis* 54:661-664). Such observations suggest that clearance of plasma t-PA, like that for certain other serum glycoproteins (Ashwell and Harford (1982) *Ann. Rev. Biochem.* 51:531-554) may be mediated through an interaction with a specific hepatic cell surface receptor, followed by internalization and degradation within the cell. The recent demonstration of a novel high affinity uptake system for recombinant t-PA on rat hepatocytes supports this hypothesis (Bakhit et al. (1987) *J. Biol. Chem.* 262:8716-8720).

There is a significant need for a modified t-PA which retains its thrombolytic effectiveness in vivo, but which is not subject to rapid degradation following its administration. Such a modified t-PA would have enhanced utility for treatment of thrombotic disorders, such as acute myocardial infraction.

DISCLOSURE OF THE INVENTION

Figure 1:
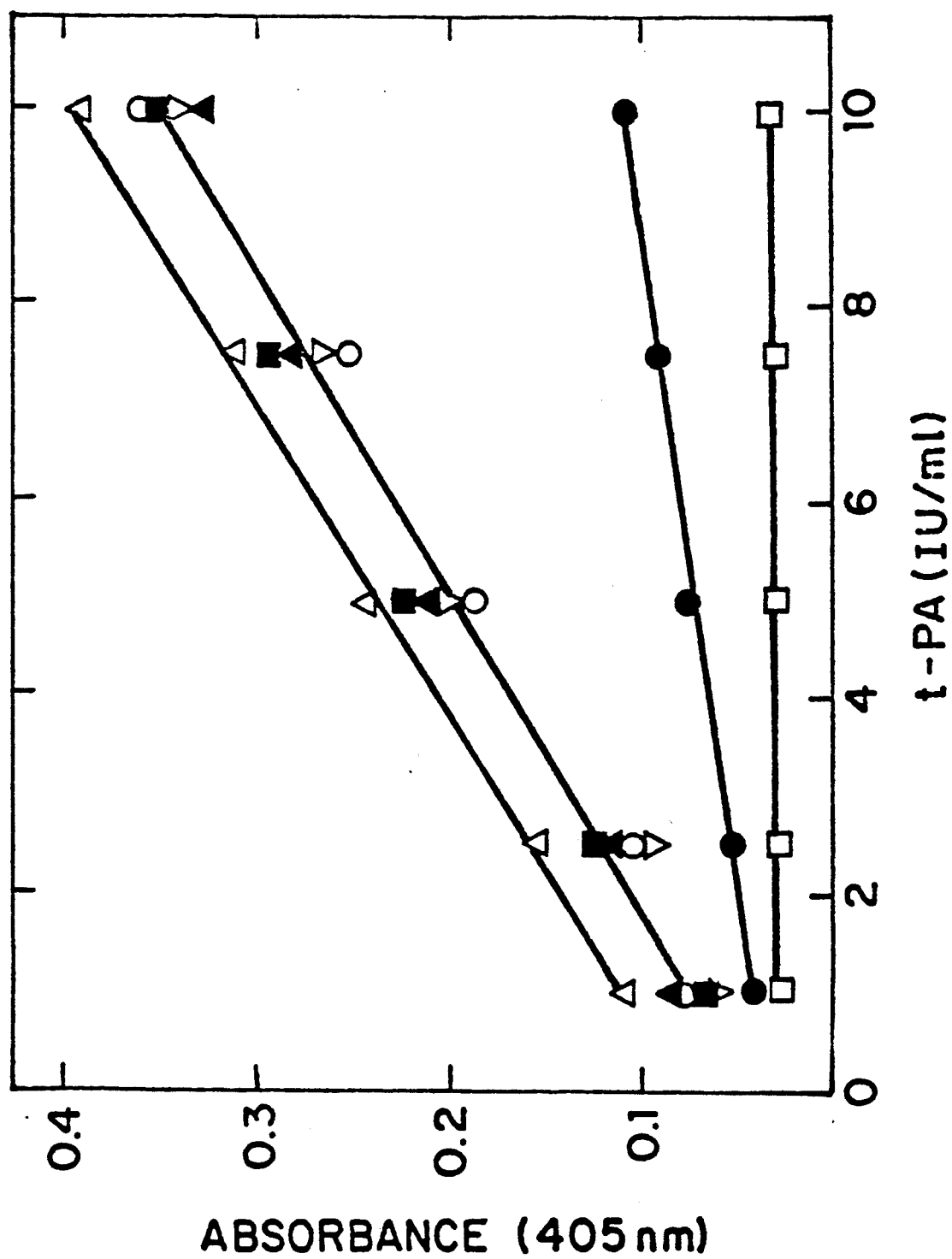
FIG. 1 shows the effects of several mAbs on the fibrin-dependent plasminogen activation activity of t-PA. Activity was determined spectrophotometrically using the chromogenic substrate S-2251 following incubation of t-PA for 1 h at 37° in the presence of: (△)AE5, (○) BA10, (□) CD2, (●) DB10, (■) EG2, (▲) MOPC-21 and (▽) no antibody. All t-PA concentrations are reported in international units (IU) by comparison with the International Reference Preparation for t-PA.

A panel of monoclonal antibodies (mAbs) directed against t-PA were generated and shown to exhibit different and useful properties. The interaction of these mAbs with t-PA was characterized, including determining their effects on t-PA functional activity and on the interaction of t-PA with its fast-acting specific inhibitor, PAI-1. These mAbs define at least three distinct epitopes on t-PA, including the catalytic site and the t-PA receptor binding site.

The specificity of the mAbs was established in ELISAs using t-PA-coated microtitre wells, and in a solid phase RIA where the binding of iodinated t-PA to the antibodies was displaced by excess unlabeled t-PA. This RIA was employed to determine binding constants for each t-PA specific antibody, which ranged from $4.9 \times 10^8 M^{-1}$ to $2.3 \times 10^9 M^{-1}$. This panel of antibodies was broadly classified into three categories based on their different effects on both the plasminogen activator activity and the amidolytic activity of t-PA, as detailed in Example 3. Antibodies AE5, BA10 and EG2, which displayed negligible or small inhibitory effects in these assays, comprise one broad class characterized by their recognition of epitopes remote from the catalytic site of t-PA. CD2, on the basis of its near total inhibition of t-PA activity in both assays, is apparently directed to an epitope at or near the catalytic site. DB10, on the basis of its partial inhibitory effect, represents a third type which is most probably directed to a determinant close to but outside of the catalytic site.

T-PA is synthesized as a single-chain protein, but is converted by plasmin into a two-chain form in which the H-chain, located at the N-terminal section of the molecule, is connected by a disulfide bond to the L-chain, at the C-terminal end (Pennica et al. (1983) *Nature* 301:214-221). Recent studies using site-specific monoclonal antibodies (Holvoet et al. (1986) *Eur. J. Biochem.* 158:173-177) and t-PA deletion mutant proteins (MacDonald et al. (1986) *Gene* 42:59-67) have unequivocally demonstrated that the L-chain of t-PA is solely responsible for the substrate specificity and the serine protease activity of the molecule. Clearly then, the epitope recognized by CD2, and probably that recognized by DB10, reside in the L-chain. Studies have also revealed that a PAI binding site on t-PA is located at or near the catalytic site on the L-chain (Van Zonnevelt et al. (1986) *J. Cell. Biochem.* 32:169-178). On the basis of this information, one would predict in advance the exact pattern of inhibition actually exhibited by this panel of antibodies on the t-PA-PAI interaction: CD2>DB10>EG2,AE5,BA10.

In its properties, therefore, CD2 resembles monoclonal antibodies generated by Loskutoff and coworkers (Schleef et al. (1986) *Thromb. Haemostasis* 56:328-332) and Collen and coworkers (Holvoet et al. (1987) *Blood* 69:284-289), both of which bound to free t-PA but not t-PA complexed to PAI. These mAbs are useful in immunoassays for t-PA in biological samples. t-PA collected from human plasma (Holvoet et al. (1987) *Blood* 69:284-289), and most cell lines (Levin (1983) *Proc. Natl. Acad. Sci. USA* 80:6804-6808) is either partially or entirely complexed with PAI(s), and the distinction between this free (active) and complexed t-PA (inactive) is important in determining fibrinolytic activity of such samples. CD2, because of its recognition of the PAI binding domain on t-PA, represents a reagent capable of distinguishing free t-PA from t-PA-inhibitor complexes, unlike antibodies AE5, BA10 and EG2.

Another application of these antibodies is for analyzing and altering the regulation of t-PA activity. The regulation of fibrinolysis in vivo is dependent on the interaction of t-PA with at least four separate proteins: plasminogen, fibrin, PAI, and a cell surface receptor (Van Zonnevelt et al. (1986) *J. Cell. Biochem.* 32:169-178). The nature of the interaction between t-PA and these four proteins has not been fully clarified as yet. Antibodies directed to each of these protein binding domains on the t-PA molecule would constitute extremely useful reagents for inhibiting these protein interactions so that their role in regulating t-PA activity can be assessed. The CD2 epitope is localized to the catalytic site of t-PA.

Although t-PA is a potent fibrinolytic agent, one drawback associated with its therapeutic use is its rapid removal from the circulation by the liver; more than 50 percent of the t-PA present in the plasma is cleared within 5 minutes after termination of the infusion. This necessitates administration of t-PA by continuous intravenous infusion over three hours in treatment of acute myocardial infarction. The recommended therapeutic dose of t-PA in humans is 100 mg, although a dose in excess of 100 mg may be required (Verstraete et al. (1985) *Lancet* 1:842-847); this is due in part to its short systemic half-life. These high doses of t-PA may be responsible for the side effects observed in t-PA-treated patients, most notably systemic hemorrhaging. In fact, official labeling for t-PA warns that a dose of 150 mg not be used because of its association with intracranial bleeding. In the present invention it is shown that modification of t-PA by formation of a complex with certain t-PA-specific mAbs to prevent recognition by the liver clearance mechanism, which apparently involves a specific hepatocyte receptor, results in an increased functional half-life for the enzyme in vivo. A t-PA with longer in vivo half-life should permit use of lower doses to achieve thrombolytic efficacy with the advantages of reduced systemic hemorrhaging, reduced proteolysis of plasma proteins, more convenient dosage regiments, including a shorter period of administration, and reduced cost per therapeutic dose. With the current cost of a course of t-PA therapy in excess of $2000, the prospect of reducing t-PA dosage is very important in allowing wider utilization of the drug.

The present invention provides monoclonal antibodies (mAbs), or portions thereof, specific for human t-PA which have the following properties: 1) the mAbs have no significant inhibitory effect (i.e., no greater than 10%) on the catalytic activity of t-PA; 2) the mAbs increase the functional half-life of t-PA in a mammal by at least 100%; 3) the mAbs have a high affinity for t-PA, i.e., a Ka with respect to t-PA of at least $1 \times 10^7$ M$^{-1}$ and preferably at least $1 \times 10^8$ M$^{-1}$. The mAbs of the invention are believed to increase the functional half-life of t-PA by inhibiting the binding of t-PA to cell surface receptors responsible for t-PA clearance. A significant degree of inhibition of the binding of t-PA to cell surface receptors, in excess of 50%, is probably necessary to prolong half-life to a clinically significant extent. Such mAbs, or portions thereof, are useful in fibrinolytic therapy by enhancing the activity of t-PA. The ability to obtain mAbs with these desired properties is unexpected and nonobvious based on our limited knowledge of t-PA's interaction with cellular receptors, and the roles of these interactions in regulating t-PA activity. In particular, it was not predictable that hepatic receptor binding could be inhibited by a mAb without inhibiting the catalytic activity of t-PA as well. Furthermore, the relative contributions of PAI and the hepatic clearance mechanisms to t-PA inactivation are still not well understood and it was not previously known that blocking hepatic cell binding without altering the binding of t-PA to PAI would in fact prolong the in vivo functional half-life of t-PA. Moreover, it should be recognized that the molecular structure of the t-PA hepatic receptor and the nature of the t-PA-receptor interaction are not well understood. Accordingly, while the mAbs of the invention are believed to prolong the functional half-life of t-PA by inhibiting hepatic clearance, the quantitative relationship between inhibition of hepatic cell binding and prolongation of t-PA half-life has not been fully elucidated, and the invention is not intended to be limited to mAbs that function by that postulated mechanism to prolong half-life.

Murine monoclonal antibodies specific to t-PA were generated and further screened for their ability to inhibit the binding of t-PA to receptors on cultured human lung fibroblasts, and on cultured human hepatoma cells. One such antibody, designated EG2, had no inhibitory effect on the catalytic activity of t-PA, as measured by in vitro functional assays. A hybridoma producing monoclonal antibody EG2 has been deposited as American Type Culture Collection Accession Number HB9690, American Type Culture Collection, 12301 Parklawn Drive, Rockville, Md. 20852. In vivo clearance studies, performed in the rabbit with either t-PA or t-PA-EG2 complexes, indicated that this antibody significantly prolonged the functional life of t-PA. In this animal model, the in vivo functional half-life of t-PA was increased from 4.6 minutes in the absence of EG2 to 15 minutes in the presence of EG2. EG2 appears to function by decreasing the hepatic clearance of t-PA by inhibiting the binding of t-PA to its receptor, without impairing its catalytic activity. Monoclonal antibodies like EG2 may be complexed with t-PA to result in a longer-lasting fibrinolytic agent. By nature of its unique antibody component, such a complex represents a novel fibrinolytic agent having enhanced utility.

The potential problem of immunogenicity when introducing murine antibodies into humans may be reduced or eliminated by: 1) utilizing smaller, less immunogenic fragments of murine antibodies such as Fab fragments (Garvey et al. (1977) *Methods in Immunology*, W. A. Benjamin, Reading, Mass.); 2) utilizing human monoclonal antibodies (Schlom et al. (1980) *Proc. Natl. Acad. Sci.* USA 77:6841–6845; Satoh et al. (1983) *N. Engl. J. Med.* 309: 217–220); or 3) utilizing human-mouse chimeric antibodies produced by genetic engineering techniques (Oi et al. (1986) *BioTechniques* 4:214–221). Furthermore, the recommended administration of t-PA (or, in this case, t-PA-mAb complex) as a single course of therapy over a relatively short period of time followed by the relatively rapid clearance from the plasma would minimize the likelihood that a significant immune response to a murine mAb, or a fragment thereof, would develop.

By complexing t-PA to a specific monoclonal antibody with the above described properties, a "second generation" t-PA with prolonged biological half-life is created. Such a molecule may have wide applications in fibrinolytic therapy by nature of its ability to moderate one of the major limitations of t-PA: its rapid clearance from the circulation. Such a t-PA-mAb complex should allow a shorter period of administration than the prolonged three hour infusion therapy currently used. Such a t-PA-mAb complex should also allow use of lower doses of t-PA to achieve local thrombolytic efficacy while reducing side effects such as systemic hemorrhaging.

Monoclonal antibodies directed to distinct epitopes located along the t-PA molecule have a number of important applications. These include the use of such mAbs in the quantification and purification of t-PA, in studying the interaction of t-PA with fibrin, plasminogen, inhibitors, and receptors, and as probes for studying the biological activity of t-PA.

DOSAGE AND ADMINISTRATION

A t-PA-mAb complex would be administered as a sterile, nonpyrogenic intravenous solution. The aqueous parenteral vehicle could be, e.g., Sterile Water for Injection USP, 0.9% Sodium Chloride for Injection USP or 5% Dextrose Injection USP. Other appropriate additives, as known to those skilled in the art of pharmaceutical formulations may be added as desired. See, for example, *Remington's Pharmaceutical Sciences*. The mAb-t-PA complex may be prepared in a stable formulation ready for administration, or for dilution in an appropriate intravenous solution. Alternatively, to increase product shelf life, the mAb and the t-PA may be individually formulated, e.g., as a sterile lyophilized powder to be reconstituted aseptically or as a buffered solution. The mAb-t-PA complex would then be prepared immediately prior to administration.

The t-PA and the mAb should be present in a 1:1 molar ratio, or with an appropriate excess of mAb so that essentially all of the t-PA will be bound. For example, a dose of 50 mg of t-PA (MW 68,000 Dalton), would require at least 110 mg of a mAb (MW approx. 150,000 Dalton). Like t-PA, the mAb-t-PA complex should preferably be administered as a single course of therapy, to be initiated as soon as feasible after diagnosis of acute myocardial infarction or other thrombotic condition to be treated. The dosage of mAb-t-PA complex required will vary depending on the extent to which the half-life of t-PA is prolonged by the particular mAb that is used. As is known to those skilled in the art, individual patient dosage will also depend on factors such as patient weight, the severity of the clinical situation, and the presence of factors which increase the risk of bleeding.

In order to obtain the rapid therapeutic blood levels required for treatment of acute myocardial infarction or other acute thrombotic episode, it may be appropriate to administer a bolus of the complex, followed by a continuous intravenous infusion for a period of time sufficient to maximize localized fibrinolysis. The use of a mAb-t-PA complex, wherein the mAb prolongs the in vivo functional half-life of t-PA, would be expected to significantly shorten the required administration time from the three hours currently recommended for t-PA alone. For example, the EG2 antibody increases the half-life of t-PA from 4.6 to 15 minutes, an increase of over 300 percent.

The following examples are intended to illustrate but not to limit the invention. Based on the instant invention it is expected that without undue experimentation one skilled in the art could obtain other monoclonal antibodies that prolong the functional half-life of t-PA without significantly reducing its catalytic activity. As used herein, t-PA means natural human t-PA, recombinant human t-PA, and functional modifications thereof.

EXAMPLE 1

Preparation of Monoclonal Antibodies Against t-PA

Balb/c mice were immunized by intraperitoneal injections with 25 μg of purified one-chain human t-PA (American Diagnostica Inc., Greenwich, Conn.) in monophosphoryl lipid A-trehalose dimycolate (MPL-TDM, RIBI Immunochem Research, Inc., Hamilton, Mont.), and boosted on a tri-weekly basis with a similar dose in TDM. Both the one-chain and two-chain forms of t-PA are active and would be expected to have similar immunogenicity. Three days after the third or fourth injection, at which time a serum antibody response was detectable, animals were sacrificed and the spleen cells fused with P3X63.Ag8.653 myeloma cells using PEG 1500 as described (Reilly et al. (1987) *Biochem. Biophys. Res. Commun.* 143:133–139). After selection in HAT medium, the supernatants were screened for specific antibody production by an ELISA using microtitre plates coated with 1 μg of t-PA per well. The bound immunoglobulins were quantified with alkaline-phosphatase-conjugated goat anti-mouse IgG (Cooper Biomedical, Malvern, Pa.). Positive hybridomas were subcloned by limiting dilution. Large quantities of the monoclonal antibodies were purified from ascites fluid, obtained in Balb/c mice, by HPLC using a Protein-A column (Bio-Rad, Richmond, Calif.). Class determination was performed with an isotyping ELISA (Bio-Rad).

Supernatants of hybridomas, resulting from four separate fusions of the P3 myeloma cells with spleen cells of t-PA-immunized Balb/c mice were screened for specific antibody production by ELISA using t-PA-coated plates. Hybridoma cells from 11 positive wells were cloned by limiting dilution, and five of these clones producing antibody to t-PA were chosen for further studies. These antibodies, designated AE5, BA10, CD2, DB10 and EG2, were classed as IgG1s in typing ELISAs.

EXAMPLE 2

Solid-Phase RIA and Determination of Antibody Association Constants

Antibody in 100 μl of culture supernatant samples was captured on Immunlon II microtitre wells (Dynatech Labs., Alexandria, Va.) that had previously been coated with goat anti-mouse Ig (Cooper Biomedical). Following washing with PBS, 100 μl of RIA buffer (0.05M Tris buffer, pH 8.5, 0.1M NaCl, 0.01M EDTA, 0.05% Tween ® 20 and 1% BSA), containing 50,000 cpms of [$^{125}$I]t-PA (Du Pont-NEN Research Products, Billerica, Mass.) and various concentrations of unlabeled t-PA were added to each well. Samples were incubated overnight at 4° C., the wells were washed and removed, and the radioactivity of each determined in a gamma counter. The association constants ($K_a$'s) of the monoclonal antibodies for t-PA were determined as described (Muller (1980) *J. Immunol. Meth.* 34:345-352) using the average of triplicate wells.

For each of the t-PA hybridomas, 100 μl of culture supernatant bound between 25 and 40% of 3 ng [$^{125}$I]t-PA in the solid phase RIA. Standard curves were then generated for each antibody using these amounts of antibody and [$^{125}$I]t-PA, and five increasing concentrations of unlabeled t-PA. Affinity constants as calculated according to the method of Muller (op. cit.) are: AE5, $4.9 \times 10^8 M^{-1}$; BA10, $7.8 \times 10^8 M^{-1}$; CD2, $2.3 \times 10^9 M^{-1}$; DB10, $8.4 \times 10^8 M^{-1}$; EG2, $1.3 \times 10^9 M^{-1}$. From standard curves, it is concluded that the sensitivity limits in immunoassays for t-PA with these antibodies ranges between approximately 1 to 10 ng of t-PA per 100 μl assay, or 10 to 100 ng of t-PA per ml of sample. With the exception of DB10, the antibodies did not discriminate between one-chain and two-chain forms of t-PA. DB10 displayed approximately ten-fold lower affinity for the two-chain species. Urokinase solutions up to 10 μl/ml did not interfere in the assay with any of the antibodies.

EXAMPLE 3

Influence of Monoclonal Antibodies on the Plasminogen Activation and Amidolytic Activity of t-PA The effects of monoclonal antibodies on the fibrin-dependent plasminogen activation activity of t-PA were determined by incubation of t-PA with a ten-fold molar excess of purified antibody for 1 h at 37° C., prior to evaluation of its activity in generating plasmin from plasminogen. For this purpose, a spectrophotometric assay (Kabi Vitrum), which measures the amidolytic activity of generated plasmin on the chromogenic substrate D-Val-Leu-lys-p-nitroanilide (S2251), was used (Zamarron et al. (1984) *J. Biol. Chem.* 259:2080-2083).

The fibrin-independent amidolytic activity of t-PA, before and after preincubation with a twenty-fold molar excess of monoclonal antibodies, was measured spectrophotometrically at 405 nm using the synthetic substrate D-Ile-Pro-Arg-NH-nitroanilide (S-2288) at 0.3 mM (Friberger (1982) *Scand. J. Chim. Lab. Invent.* 42:1-98).

The plasminogen activator activity of t-PA, before and after preincubation with a ten-fold molar excess of monoclonal antibodies, was measured spectrophotometrically relying on the chromogenic substrate S-2251. In view of the comparable affinities of the antibodies for t-PA, this same twenty-fold excess was used for all the antibodies. On the basis of the data shown in FIG. 1, this panel of antibodies could be broadly subdivided into three classes: complete inhibitors (CD2), partial inhibitors (DB10), and those with limited effect on the activity (AE5, BA10 and EG2). As used herein, "limited effect" means less than 10% inhibition. An irrelevant IgG1 antibody (MOPC-21) had no effect on t-PA activity in this assay indicating the specificity of the t-PA antibody effects.

Figure 2:
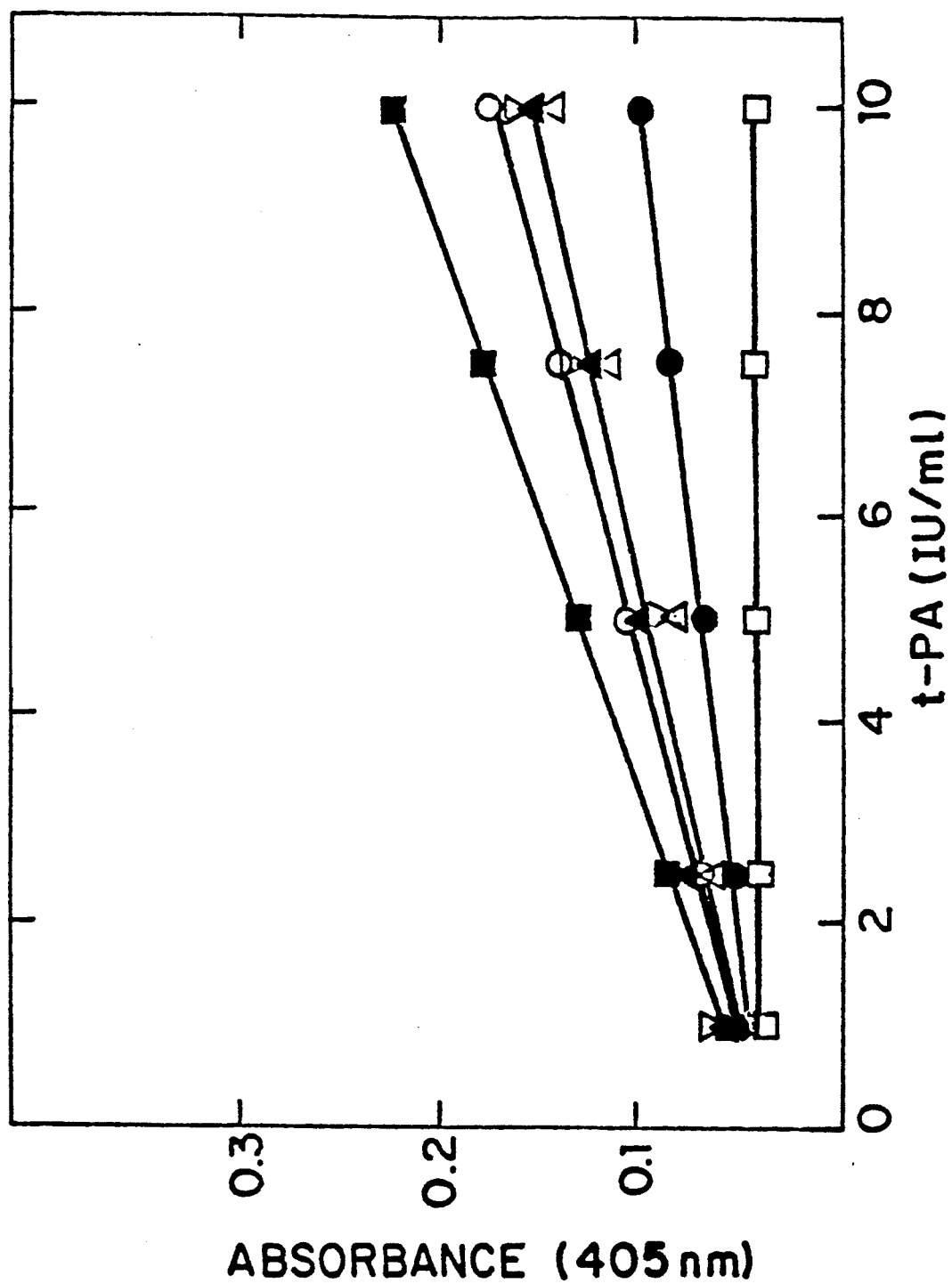
FIG. 2 shows the effects of several mAbs on the fibrin-independent amidolytic activity of t-PA. Activity was determined spectrophotometrically using the chromogenic substrate S-2288 following incubation of t-PA for 1 h at 37° in the absence or presence of the various antibodies. Symbols are the same as described in the legend to FIG. 2.

Since the plasminogen activation activity of t-PA is greatly enhanced by fibrin, inhibitors of this activity may be acting at either of two sites on t-PA: the catalytic site or the fibrin binding domain. To investigate these possibilities for the antibodies CD2 and DB10, and to examine further the epitopes recognized by this panel of monoclonal antibodies, the fibrin-independent amidolytic activity of t-PA following incubation with each of the antibodies was measured. This assay relies on the ability of t-PA to cleave the chromogenic substrate S-2288, and activity is not dependent on the presence of fibrin. FIG. 2 shows a similar pattern was observed in this assay as in the S-2251 assay; CD2 totally inhibited the amidolytic activity of t-PA; DB10 was partial inhibitory; while AE5, BA10 and the control antibody MOPC-21 had negligible effects. EG2 slightly enhanced the amidolytic activity of t-PA.

The results of both chromogenic assays therefore suggest that CD2 recognizes an epitope on t-PA at or near the catalytic site while DB10 recognizes one somewhat removed from this site. The other antibodies in this panel appear to bind at epitopes remote from the active site.

EXAMPLE 4

Effect of Antibodies on the Binding of t-PA to its Fast-acting Inhibitor, PAI-1

PAI-1, purified from the human fibrosarcoma cell line HT-1080, and a murine monoclonal antibody against PAI-1 were purchased from American Diagnostica Inc. (Greenwich, Conn.). The following protocol was developed to determine the ability of antibodies to influence the binding of t-PA to PAI-1. 100 μl of a 500 ng/ml solution of PAI-1 in 0.1M Tris, pH 8.0 was added to microtitre wells that had been previously coated with 1 μl of the PAI-1 monoclonal antibody and blocked with BSA. Following overnight incubation at 4° C. and washing with Tris buffer, 3 ng of $^{125}$It-PA (50,000 cpm) that had been preincubated in the absence or presence of 1 μg of antibody for 1 h at 37° C. was added to each well. After 1 h, wells were washed, removed, and the radioactivity determined in a gamma counter. Triplicate wells were performed for each antibody.

To examine the effects of the antibodies on the t-PA-PAI-1 interaction, we utilized a monoclonal antibody to capture PAI on microtitre wells. This particular antibody, which is directed to a region on the PAI-1 not involved in its binding to t-PA, was utilized to minimize potential effects on protein conformation in immobilizing the PAI directly on the plastic wells. The ability of [$^{125}$I]t-PA, either free or complexed with the t-PA monoclonal antibodies, to bind to the PAI captured on microtitre wells was then examined; results are presented in Table 1. The pattern of the antibody effects on this interaction was similar to that observed in the functional assays, with CD2 pretreatment resulting in the greatest inhibition followed by DB10. Addition of large concentrations of unlabeled t-PA or urokinase resulted in near total inhibition of the [$^{125}$I]t-PA-PAI interaction, as would be expected based on the ability of PAI-1 to bind both these proteins. Negligible binding of [$^{125}$I]t-PA was observed in wells coated with only the monoclonal antibody to PAI-1.

TABLE 1

Effect of Monoclonal Antibodies on the Binding of t-PA to PAI-1

[$^{125}$I]t-PA, pretreated for 1 h at 37° C. with the different antibodies, was evaluated for its ability to bind PAI-1 captured on microtitre wells. Data is expressed as % binding relative to the value observed with [$^{125}$I]t-PA which was incubated for 1 h at 37° C. but in the absence of antibody. Unlabeled t-PA and urokinase were included at concentrations of 5 μg in the control wells. Each value represents the mean from triplicate wells, ± S.D.

| Antibody | % Binding |
| --- | --- |
| AE5 | 86 ± 9 |
| BA10 | 91 ± 2 |
| CD2 | 9 ± 1 |
| DB10 | 35 ± 4 |
| EG2 | 70 ± 2 |
| MOPC-21 | 100 ± 8 |
| t-PA | 8 ± 1 |
| urokinase | 8 ± 2 |

EXAMPLE 5

Inhibition of Binding of [$^{125}$I]t-PA to WI-38 Human Fibroblasts by mAb EG2

The human lung fibroblast cell line, WI-38, was obtained from the American Type Culture Collection. Cells were maintained in minimal essential medium containing penicillin, streptomycin, and 10% fetal calf serum. Cells were grown to confluence in 24-well tissue culture plates. Plates were washed three times quickly with binding buffer (serum-free medium containing 1 mg/ml of bovine serum albumin) at 25°, using vacuum suction to remove the supernatant, and 200 μl of binding buffer containing 0.2 nM [$^{125}$I]t-PA and competitors, where applicable, were added to each well. Following the incubation period, usually at 25° C., cells were washed three times quickly with 4° C. phosphate buffered saline containing 1 mg/ml of bovine serum albumin. One-half ml of a 1×trypsin solution was then added to each well to dislodge the cells, which were collected into tubes and counted in a gamma-ray counter. Specific binding was calculated by subtracting the counts bound in the presence of 10$^{-7}$M unlabeled t-PA. Cell numbers were obtained by counting trypsinized cell suspensions in a hemocytometer and binding data was calculated as fmols bound per 10$^6$ cells. All data points are the average value of triplicate wells which varied less than 5%. One-chain t-PA was used in all binding experiments except where indicated.

The specific binding of t-PA to monolayers of WI-38 human lung fibroblasts and to HepG2 human hepatoma cells (Example 6) is strongly suggested to involve specific receptor-ligand interaction in that the process was saturable, specific in nature, and of high affinity.

To examine the effects of different mAbs on the binding of [$^{125}$I]t-PA to WI-38 fibroblasts, the [$^{125}$I]t-PA was incubated with approximately 5 μg of the appropriate mAb for 30 min at 25° C. prior to its addition to wells of WI-38 fibroblasts for the 1 h binding period as described above. The percentage of inhibition induced by each mAb was determined relative to the binding observed with [$^{125}$I]t-PA that was pretreated for 30 min at 25° C. in the absence of mAb. As shown in Table 2, the mAbs EG2 and AE5 inhibited binding substantially, while mAbs BA10 and BG8 had much less inhibitory effects. An irrelevant mAb, MOPC-21, had no inhibitory effect on [$^{125}$I]t-PA binding to WI-38 fibroblasts.

TABLE 2

Effect of Monoclonal Antibodies on the Binding of [$^{125}$I]t-PA to WI-38 Human Fibroblasts

| Antibody | % Inhibition of Binding |
| --- | --- |
| EG2 | 97 |
| AE5 | 95 |
| BA10 | 27 |
| BG8 | 12 |
| MOPC-21 | 0 |

EXAMPLE 6

Inhibition of Binding of [$^{125}$I]t-PA to HepG2 Human Hepatoma Cells

Previous studies have described specific binding of t-PA to rat hepatocytes (Zamarron et al. *J. Biol. Chem.* 259:2080-2083) and human endothelial cells (Andreasen et al. (1986) *J. Biol. Chem.* 261:7644-7651). The hepatocyte binding site has been implicated in mediating the clearance of t-PA from the circulation by promoting its binding, internalization and degradation by lysomal enzymes (Zamarron et al. *J. Biol. Chem.* 259:2080-2083).

Since certain mAbs to t-PA inhibited t-PA's binding to WI-38 fibroblasts, their effects on t-PA binding to an established human hepatoma line, HepG2, were evaluated. To examine the effects of mAbs on the binding of [$^{125}$I]t-PA to human hepatoma cells, the procedures described in Example 5 were utilized except that HepG2 cells were utilized instead of WI-38 fibroblasts. The cells were purchased from American Type Culture Collection. Table 4 shows that EG2 and AE5 were both capable of blocking [$^{125}$I]t-PA binding to these cells.

TABLE 4

Effect of Monoclonal Antibodies on the Binding of [$^{125}$I]t-PA to HepG2 Human Hepatoma Cells

| Antibody | % Inhibition of Binding |
| --- | --- |
| EG2 | 61 |
| AE5 | 33 |
| BA10 | 0 |

EXAMPLE 7

Figure 3:
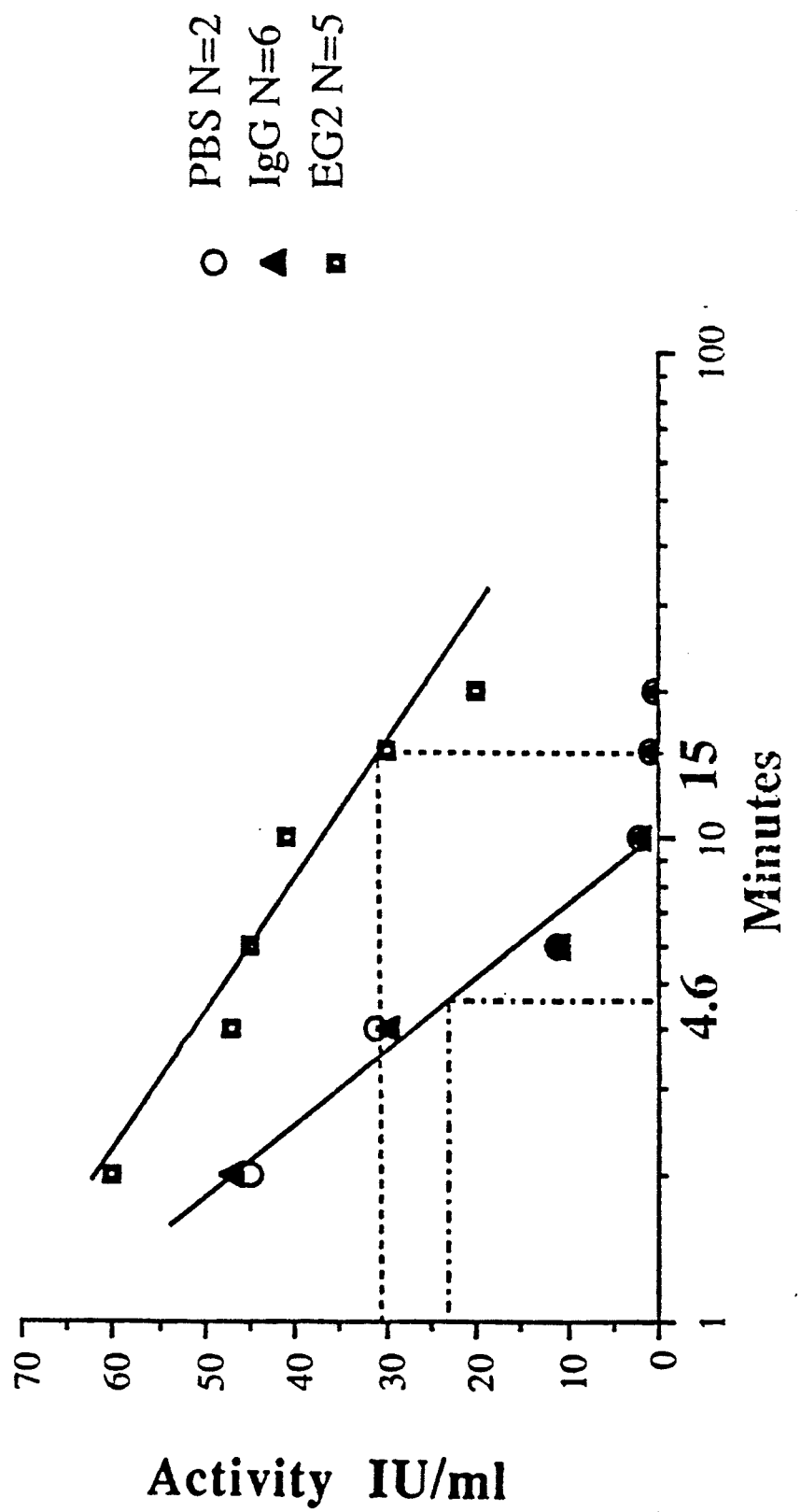
FIG. 3 shows the level of t-PA activity (using the S-2251 substrate) in arterial blood samples of a rabbit at times following the intravenous injection of t-PA (○), t-PA containing mAb IG12 (▲), and t-PA containing mAb EG2 (■). The in vivo functional half-life of t-PA is indicated by the dashed lines.

Effect of mAb EG2 on the Clearance of t-PA Injected Into Rabbits 22 gauge intracaths were injected into ear arteries of the test rabbits. 20,000 I.U. (0.02 mg) of t-PA was incubated with 0.4 mg of the mAb EG2, mAb BA10, or an irrelevant mAb not directed to t-PA (IG12), for 30 min at 25° C. The mAb t-PA solutions were then injected intravenously, through a lateral ear vein, into rabbits. At 2, 4, 6, 10, 15 and 20 min after injection, arterial blood samples were collected from each rabbit, and stored frozen prior to activity determinations. The plasminogen activation activity of t-PA in each sample was then determined by means of the S2251 chromogenic assay described in Example 3. FIG. 3 shows that the half-life of uncomplexed t-PA as well as the t-PA mixed with the control mAb IG12, based on functional activity, was approximately 4.6 min. T-PA complexed with the mAb EG2, however, displayed a much greater half-life of approximately 15 min. (mAb BA10 had no effect on in vivo half-life functional of t-PA. Furthermore, EG2 did not inhibit the functional activity of t-PA. MAb BA10 had no effect on in vivo functional half-life of t-PA. Based on data presented in Examples 4, 5 and 6, the increased in vivo half-life of t-PA complexed to EG2 is attributable, at least in part, to EG2's ability to inhibit binding and degradation of t-PA by liver cells. A t-PA-EG2 complex therefore represents a novel form of t-PA with the desirable properties of prolonging in vivo its half-life without impairing its functional activity, i.e., EG2 prolongs the in vivo functional half-life of t-PA. Such an agent would be a particularly attractive therapeutic for treatment of emergency thrombotic disorders.

We claim:

1. A monoclonal antibody, or Fab fragment thereof, which immunologically complexes with tPA, having the following properties: complexes with tPA with an association constant, $K_a$, of at least $10^8 M^{-1}$; complexes with tPA without decreasing the fibrin-dependent plasminogen activator activity of tPA by more than 10% relative to tPA not complexed with monoclonal antibody; inhibits the binding of tPA to the tPA-binding receptor on the surface of HepG2 human hepatoma cells by at least 50% relative to tPA not complexed with monoclonal antibody; when noncovalently complexed with tPA, increases the in vivo half-life of the fibrin-dependent plasminogen activation activity of tPA by at least 2-fold relative to tPA not complexed with monoclonal antibody.

2. A murine monoclonal antibody according to claim 1.

3. A hybridoma which produces a monoclonal antibody of claim 1.

4. A hybridoma which produces a monoclonal antibody of claim 2.

5. A hybridoma of claim 4 having the identifying characteristics of the cell line deposited as American Type Culture Collection Designation Number HB9690, producing monoclonal antibody designated EG2.

6. A murine monoclonal antibody designated EG2, produced by a hybridoma of claim 5.

* * * * *